May 7, 1974
F. PAGANELLI
Plant Pat. 3,541
APPLE TREE
Filed Jan. 29, 1973
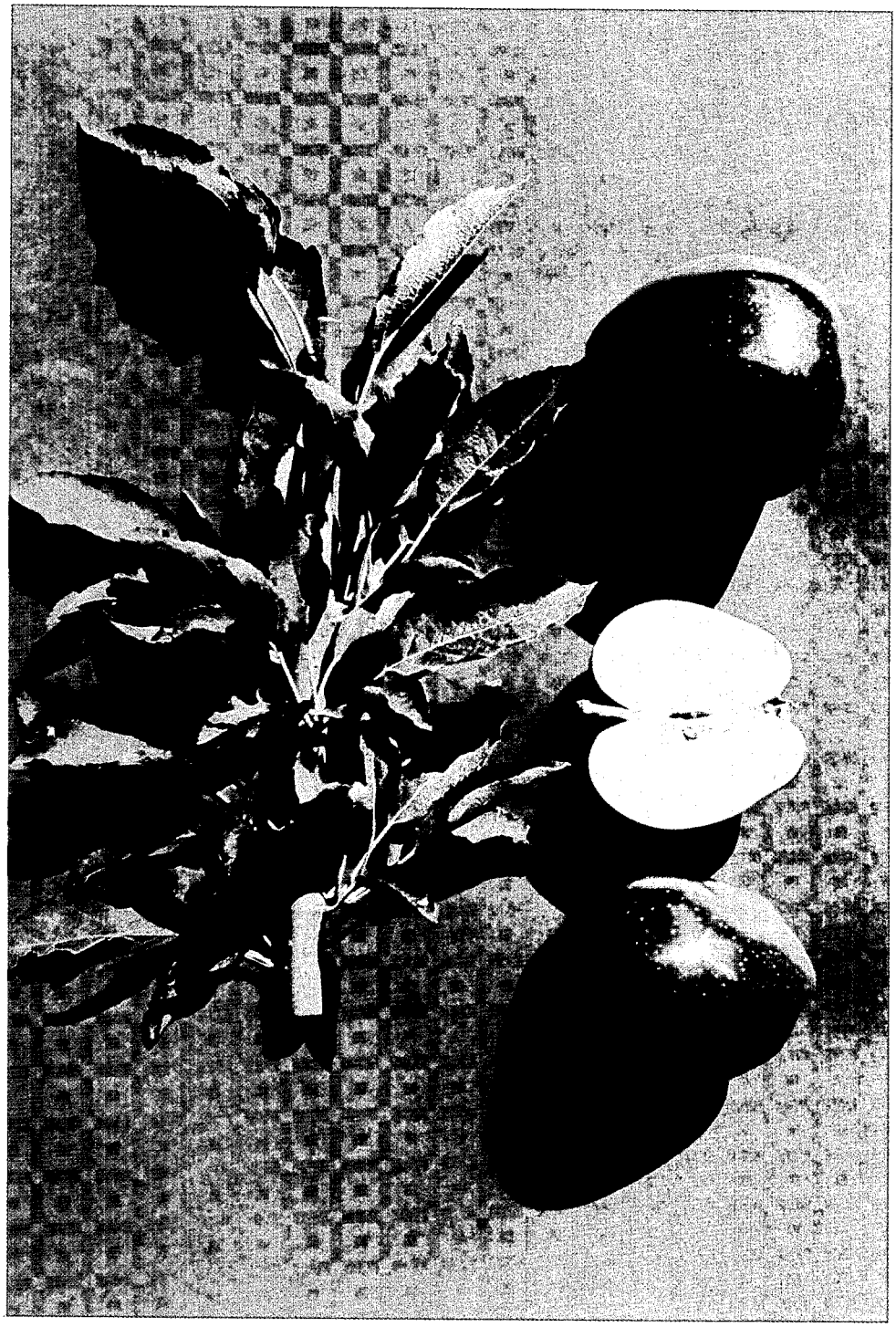

United States Patent Office

Plant Pat. 3,541
Patented May 7, 1974

3,541
APPLE TREE

Frank Paganelli, Yakima, Wash., assignor to Stark Bro's Nurseries & Orchards Co., Louisiana, Mo.

Filed Jan. 29, 1973, Ser. No. 327,824
Int. Cl. A01h 5/03
U.S. Cl. Plt.—35 1 Claim The present invention relates to a new and distinct variety of apple tree which was discovered by me as a single limb mutation originated from a bud sport of the famous apple variety known as "Delicious" (unpatented) which has been widely distributed in the trade by the assignee hereof under the registered trademark "Starking," said discovery having been made by me in my cultivated orchard located at Yakima, Wash.

At the time of my discovery, I was growing in my orchard aforementioned a block of trees of the "Starking Delicious" apple variety, among other varieties, and during one of my routine inspections of this orchard late in the harvest season, I noticed that the fruit borne on one limb of one tree in the "Starking Delicious" block retained a bright cherry red blush well beyond the coloring of the other fruit, and even longer than the color of the fruit of the "Red Delicious" apple variety (Plant Pat. No. 1,565) which has been extensively distributed by my assignee under the registered trademark "Starkrimson," and the fruit of which usually becomes dark red when left on the tree through full maturity. Accordingly, I carefully preserved the sport limb and subsequently reproduced the same by graftings, as made by me in my orchard at Yakima. My continued observations of the original sport limb and its progeny derived therefrom by graftings as aforementioned, confirmed the unusual fruit coloring habit as described in the foregoing and have convinced me that my new sport is a new and distinct variety as evidenced by the following unique combination of principal characteristics which are particularly outstanding therein, and which distinguish the same from its parent variety, as well as from all other apple varieties of which I am aware:

(1) A spur type and general habit of tree growth similar to that of the apple variety "Starkrimson Red Delicious";
(2) The production of fruit which is similar in shape, size and flavor to the fruit of "Starkrimson Red Delicious"; and
(3) A distinctive and attractive bright cherry red fruit color which develops as a blush like the fruit of "Starkrimson Red Delicious," but which is retained throughout the full harvest season contrary to other varieties, including "Starkrimson Red Delicious," which become a very dark red fruit color when fully tree-ripened.

The accompanying drawing shows typical specimens of the foliage and fruit of my new apple variety, with one of the fruit specimens being shown in cross-section, and all as depicted in color.

The following is a detailed description of the new variety, with color terminology in accordance with Ridgway's Color Standards and Nomenclature (hereinafter abbreviated as (R)), and the Horticulture Colour Guide (hereinafter abbreviated as (HCG)), except where general color terms of ordinary dictionary significance are obvious:

Locality where grown and observed: Yakima, Wash.
Parentage: Sport of "Starking Delicious."
Dates of first and last pickings: About Sept. 20 and Oct. 2, respectively.
Tree: Medium small; medium vigorous; upright; tall; dense; rapid growing; hardy; very productive; regular bearer.

*Trunk*—Medium stockiness; medium smoothness.

*Branches.*—Medium thickness; smooth; many spurs on limbs. Color—Diamine Brown, Plate XIII, Color No. 3′, tone m (R). Lenticels—Medium few in number; medium small.

*Leaves.*—Medium large; medium wide; medium long; ovate; taper-pointed; thick; rugose. Length—About 3½ inches. Width—About 2⅛ inches. Color—Ivy Green, Plate 0960, page 187, Vol. 2 (HCG). Margin—Coarsely serrate. Petiole—Medium long (about 1 inch); thick.

Flowers: Medium early.

*Dates of first and full bloom.*—About Apr. 20 and Apr. 25, respectively.

*Color.*—White, with tinge of Carmine, Plate 21/3, page 21, Vol. 1 (HCG).

Fruit:

*Maturity when described.*—Eating ripe (about Nov. 7).

*Size.*—Uniform. Axial diameter—From about 3⅜ inches to 3½ inches. Transverse diameter—From about 3 inches to 3¼ inches.

*Form.*—Conical; angular.

*Cavity.*—Symmetrical; flaring toward apex; undulate; pubescent toward apex. Depth—About ⅝ inch. Breadth—About 1¼ inches. Markings—Buffy Olive, Plate XXX, Color No. 21″, tone k (R).

*Basin.*—Symmetrical; abrupt at base; flaring wide base; furrowed; glabrous. Depth—About ¾ inch. Breadth—About 1¼ inches. Markings—None.

*Stem.*—Medium Stout; pubescent. Length—About 15/16 inch. Breadth—About 3/32 inch. Markings—None.

*Calyx.*—Closed; segments persistent; broadly lanceolate; acute; approximate; prostrate; reflexed from base at apex; converged from base toward center; connivent; both outer and inner surfaces pubescent.

*Eye.*—Small.

*Skin.*—Thick; tough; smooth; glossy; waxed. Dots—Obscure; many; small; depressed; circular. Color of dots—White, Plate LIII (R). Distribution—Most numerous toward basin. Color markings—Blushed; self-colored. Color—Cardinal Red, Plate 822, page 168, Vol. 2 (HCG). Scarfskin—Wanting. General color effect—Solid bright cherry red.

*Flesh.*—Juicy. Color—Satiny white, with greenish tint. Texture—Firm; fine; crisp. Flavor—Mild. Quality—Good.

*Core.*—Median. Bundle area—Medium small; oblate; symmetrical; acute at base. Bundles—Inconspicuous; in one whorl. Color—Green-tinged. Core lines—Clasping. Cross section—Indistinct. Carpellary area—Indistinct; small. Calyx tube—Glabrous toward base; funnel form. Stem of funnel—Long. Depth of tube to shoulder—About ¼ inch. Entire depth—About ½ inch. Styles—Present; united toward base; pubescent toward base. Stamens—In one whorl; marginal. Seed cells—Axile; closed. Cell walls—Approximate; thin; tough. Length—About ⅝ inch. Breadth—About 5/16 inch. Longitudinal section—Broadly ovate; obtuse at apex. Surface—Tufted. Cross section—Narrow.

Seeds: From 4 to 7 and usually all perfect; no more than 2 per cell.

*Length.*—About 9/32 inch.

*Breadth.*—About 3/16 inch.

*Form.*—Acute.

*Color.*—Chestnut, Plate II, Color No. 9, tone m (R).

Use: Market; dessert.

Keeping quality: Good; about 120 days in ordinary storage.

I claim:

1. A new and distinct variety of apple tree, substantially as herein shown and described, characterized particularly as to novelty by the unique combination of a spur type and general habit of tree growth similar to that of the apple variety "Starkrimson Red Delicious," the production of fruit which is similar in shape, size and flavor to the fruit of "Starkrimson Red Delicious," and a distinctive and attractive bright cherry red fruit color which develops as a blush like the fruit of "Starkrimson Red Delicious," but which is retained throughout the full harvest season contrary to other varieties, including "Starkrimson Red Delicious," which become a very dark red fruit color when fully tree-ripened.

No references cited.

ROBERT E. BAGWILL, Primary Examiner